United States Patent [19]

Sanderson et al.

[11] Patent Number: 5,171,909
[45] Date of Patent: * Dec. 15, 1992

[54] SYNTHETIC LUBRICANT BASE STOCKS FROM LONG-CHAIN VINYLIDENE OLEFINS AND LONG-CHAIN ALPHA- AND/OR INTERNAL-OLEFINS

[75] Inventors: John R. Sanderson, Leander; Edward T. Marquis, Austin, both of Tex.

[73] Assignee: Texaco Chemical Company, White Plains, N.Y.

[*] Notice: The portion of the term of this patent subsequent to Oct. 1, 2008 has been disclaimed.

[21] Appl. No.: 577,385

[22] Filed: Sep. 4, 1990

[51] Int. Cl.$^5$ .............................................. C07C 2/02
[52] U.S. Cl. .................................. 585/255; 585/533; 585/12
[58] Field of Search ........................ 585/12, 255, 533

[56] References Cited

U.S. PATENT DOCUMENTS

| | | |
|---|---|---|
| 2,951,087 | 8/1960 | Hauser et al. |
| 3,412,039 | 11/1968 | Miller |
| 3,432,571 | 3/1969 | Noddings et al. |
| 3,459,815 | 8/1969 | Noddings et al. |
| 3,845,150 | 10/1974 | Toning-Yuan et al. |
| 3,876,720 | 4/1975 | Heilman et al. |
| 4,153,638 | 5/1979 | Bercik et al. |
| 4,214,111 | 7/1980 | Kitamura et al. |
| 4,299,730 | 11/1981 | Sommer et al. |
| 4,351,980 | 9/1982 | Reusser et al. |
| 4,380,509 | 4/1983 | Sommer et al. |
| 4,420,646 | 12/1983 | Darden et al. |
| 4,456,779 | 6/1984 | Owen et al. |
| 4,480,142 | 10/1984 | Cobb |
| 4,531,014 | 7/1985 | Gregory et al. |
| 4,604,491 | 8/1986 | Dressler et al. |
| 4,808,559 | 2/1989 | Sommer et al. |
| 4,827,064 | 5/1989 | Wu |
| 4,879,425 | 11/1989 | Kukes et al. |

FOREIGN PATENT DOCUMENTS

1489646 10/1977 United Kingdom.

OTHER PUBLICATIONS

Kuliev et al., "Preparation of High-Viscosity Synthetic Lubericants Using an Aluminosilicate Catalyst", Institute of Petrochemical Processes of the Acadamy of Sciences of the Azerbaidzhan SSR, *Azerbaidzhan Naptiano. Khoziaistro.*, 1983, No. 4, pp. 40-43.

Figueras, "Pillared Clays as Catalysts", *Catal. Rev. Sci. Eng.*, 30(3), pp. 457-499 (1988).

Friedlander, "Organized Polymerization I. Olefins on a Clay Surface", *Journal of Polymer Science:* Part C, No. 4, pp. 1291-1301.

Friedlander et al., "Organized Polymerization, III, Monomers Intercaleted in Montmoullonite", Polymer Letters, vol. 2, pp.475-479 (1964).

"Interealated Catalysts and Pillar of Clays", from a Process Evaluation/Research Planning Report by Chem. Systems, titled Catalysts:Selected Developments, 84-3, pp. 239-249 (Dec. 1985).

Bolan, "Synthetic Lubricant Base Stochs", Process Economics Program Report No. 125A by CRI International, Apr. 1989 and Supplement A, (Sep. 1989).

"Synthetic Lubricants from Internal Olefins", Process Evaluation/Research Planning Report by Chem. Systems, 84-Q-1, pp. 17-45.

Adams, "Synthetic Organic Chemistry Using Pillared, Cation-Exchanged and Acid-Treated Montmouillonite Catalysts—A Review", *Applied* Clay Science, 2 (1987) pp. 309-342.

Adams et al., "Clays as Selective Catalysts in Organic Synthesis", *Journal of Inclusion Phenomena*, vol. 5, (1987), pp. 663-674.

Primary Examiner—Patrick P. Garvin
Assistant Examiner—E. D. Irzinski
Attorney, Agent, or Firm—Jack H. Park; Kenneth R. Priem; Russell R. Stolle

[57] ABSTRACT

A process is disclosed for preparing synthetic lubricant base stocks. Synthetic lubricant base stocks may be prepared in good yield by oligomerizing long-chain olefins using certain acidic calcium montmorillonite clay catalysts. When long-chain vinylidene olefin and long-chain alpha- and/or internal-olefin are co-oligomerized, a synthetic lubricant base stock having a lower pour point is obtained.

20 Claims, No Drawings

SYNTHETIC LUBRICANT BASE STOCKS FROM LONG-CHAIN VINYLIDENE OLEFINS AND LONG-CHAIN ALPHA- AND/OR INTERNAL-OLEFINS

CROSS-REFERENCE TO RELATED APPLICATIONS

This application is related to the following co-pending U.S. patent applications: Ser. No. 07/500,631, filed Mar. 28, 1990, which relates to the preparation of synthetic lubricant base stocks by oligomerizing linear olefins by means of certain acidic montmorillonite clays; Ser. No. 07/516,931, filed Apr. 30, 1990, which relates to the preparation of synthetic lubricant base stocks by oligomerizing certain mixtures of internal- and alpha-olefins by means of certain acidic montmorillonite clays; Ser. No. 07/516,870, filed Apr. 30, 1990, which relates to synthetic lubricant base stocks made by oligomerizing linear olefins by means of certain aluminum nitrate-treated acidic montmorillonite clays; Ser. No. 07/522,941, filed May 14, 1990, which relates to the preparation of synthetic lubricant base stocks by co-oligomerizing propylene and long-chain alpha-olefins by means of certain acidic montmorillonite clay catalysts; Ser. No. 07/525,807, filed May 21, 1990, which concerns synthetic lubricant base stocks made by co-oligomerizing 1,3-di-isopropenyl benzene and long-chain alphaolefins by means of certain acidic montmorillonite clay catalysts; Ser. No. 07/531,172, filed May 31, 1990, which concerns synthetic lubricant base stocks having an improved pour point; Ser. No. 07/534,080, filed Jun. 6, 1990, which concerns synthetic lubricant base stocks having an improved viscosity; Ser. No. 07/536,906, filed Jun. 12, 1990, which concerns synthetic lubricant base stocks made by co-reacting olefins and anisole or like compounds; Ser. No. 07/545,260, filed Jun. 28, 1990, which concerns mixtures of oligomers and certain alkylated aromatics as synthetic lubricant base stocks; and Ser. No. 07/551,969, filed Jul. 12, 1990, which concerns a process for oligomerizing olefins using phosphorous-containing acid on montmorillonite clay. The totality of each of these previously filed applications is incorporated herein by reference.

BACKGROUND OF THE INVENTION

1. Field of the Invention

The invention relates to the preparation of synthetic lubricant base stocks, and more particularly to synthetic lubricant base stocks having a low pour point.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal- and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_6$ raises environmental concerns. Thus, a method for oligomerizing long-chain olefins using a non-hazardous, non-polluting catalyst would be a substantial improvement in the art.

Kuliev et al. attempted to prepare synthetic lubricants by oligomerizing long-chain ($C_9$–$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40–43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants discovered that it is possible to prepare synthetic lubricant base stocks in good yield by oligomerizing long-chain olefins using certain acidic montmorillonite clay catalysts. Applicants found that a high conversion of long-chain olefin to dimer, trimer, and tetramer may be obtained with formation of very little concomitant hydrogen redistribution by-product by using an acidic calcium montmorillonite clay having a moisture content ranging up to about 20 wt. %, a residual acidity in the range of about 3 to about 30 mg KOH/g (when titrated to a phenolphthalein end point), and a surface area of about 300 M²/g or greater. In addition to being excellent catalysts, these clays are non-hazardous and non-polluting.

With respect to the present invention, Applicants have found, surprisingly, that synthetic lubricant base stocks having a lower pour point may be obtained where the oligomers are prepared by co-oligomerizing a mixture of (1) a long-chain vinylidene olefin and (2) a long-chain olefin selected from the group consisting of alpha-olefins and internal-olefins. U.S. Pat. No. 4,214,111 to Kitamura et al. discloses co-polymerizing higher alpha-olefins with a vinylidene olefin. However, the vinylidene olefin is a shorter-chain olefin, selected from the group consisting of isobutylene and di-isobutylene, and the catalyst employed is an aluminum halide catalyst, which may be corrosive. Applicants' process achieves a high conversion of olefin to oligomers incorporating higher molecular weight vinylidenes using a more easily handled catalyst.

SUMMARY OF THE INVENTION

The invention relates to a process for the preparation of synthetic lubricant base stocks, comprising co-oligomerizing a mixture of (1) a $C_{10}$ to $C_{24}$ vinylidene olefin and (2) a $C_{10}$ to $C_{24}$ olefin selected from the group consisting of alpha-olefins and internal-olefins, in the presence of an acidic montmorillonite clay having a moisture content ranging up to about 20 wt. %, a residual acidity in the range of about 3 to about 30 mg KOH/g, and a surface area of about 300 m²/g or greater.

DESCRIPTION OF THE PREFERRED EMBODIMENTS

Applicants discovered that synthetic lubricant base stocks may be prepared in good yield by oligomerizing long-chain olefins using certain acidic montmorillonite clay catalysts. Applicants have further discovered that the pour point of these synthetic lubricant base stocks is improved when the olefin feed comprises a mixture of long-chain vinylidene olefin and long-chain alpha- and/or internal-olefin. Preferably, from about 5 to about 40 wt. % of the mixture of starting materials comprises vinylidene olefin. More preferably, from about 15 to about 30 wt. % of the mixture of starting materials comprises vinylidene olefin. It is especially preferred that about 20 wt. % of the starting materials be vinylidene olefin.

The olefin monomer feed stocks useful in the present invention include compounds comprising (1) alpha-olefins having the formula $R''CH=CH_2$, where $R''$ is an alkyl radical of 8 to 22 carbon atoms; (2) internal olefins having the formula $RCH=CHR'$, where R and R' are the same or different alkyl radicals of 1 to 21 carbon atoms; and (3) vinylidene olefins having the formula

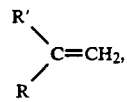

where R and R' are the same or different alkyl radicals of 1 to 21 carbon atoms, provided that the total number of carbon atoms in any one olefin (whether alpha, internal, or vinylidene) shall be within the range of 10 to 24, inclusive. A preferred range for the total number of carbon atoms in any one olefin molecule is 14 to 18, inclusive. An especially preferred range is 14 to 16, inclusive. Mixtures containing vinylidene olefins and internal- and alpha-olefins may be used, as well as mixtures containing vinylidene olefins and either internal- or alpha-olefins. However, the greatest improvement in pour point verses base stocks prepared without the inclusion of vinylidene olefin is observed when base stocks prepared from alpha-olefins alone are compared with base stocks prepared from mixtures which include vinylidene olefins. Only a small improvement is observed over base stocks which include a substantial percentage of internal olefin. Mixtures containing olefins having different numbers of carbon atoms may be used, provided that the total number of carbon atoms in any one olefin shall be within the range of 10 to 24, inclusive. The vinylidene olefins and alpha- and internal-olefins useful in the present invention may be obtained by processes well-known to those skilled in the art and are commercially available.

The oligomerization reaction may be represented by the following general equation:

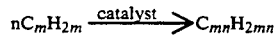

where n represents moles of monomer and m represents the number of carbon atoms in the monomer. Thus, for example, the oligomerization of 1-decene, as well as the co-oligomerization of vinylidene decene and alpha and-/or internal-decene, may be represented as follows:

The reactions occur sequentially. Initially, olefin monomer reacts with olefin monomer to form dimers. The dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The catalysts used to effect this reaction in the present invention are certain silica-alumina clays, also called aluminosilicates. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties which afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

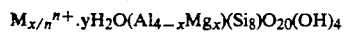

$$M_{x/n}{}^{n+} \cdot yH_2O(Al_{4-x}Mg_x)(Si_8)O_{20}(OH)_4$$

where M represents the interlamellar (balancing) cations, normally sodium or lithium; and x, y and n are integers.

Montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Applicants have discovered that certain acid-treated montmorillonite clay catalysts are particularly effective for preparing synthetic lubricant base stocks in good yield by oligomerizing long-chain olefins. These clays are acidic calcium montmorillonite clays having a moisture content ranging up to about 20 wt. %, a residual acidity in the range of about 3 to about 30 mg KOH/g (when titrated to a phenolphthalein end point), and a surface area of about 300 m²/g or greater. Illustrative examples include Filtrol grade 24, having a moisture content of 12 wt. %, a residual acidity of 8.5 mg KOH/g, and a surface area of 425 m²/g; Filtrol grade 124, having a moisture content of 2 wt. %, a residual acidity of 7.0 mg KOH/g, and a surface area of 400 m²/g; Filtrol grade 13, having a moisture content of 16 wt. %, a residual acidity of 15 mg KOH/g, and a surface area of 300 m²/g; Filtrol grade 113, having a moisture content of 4 wt. %, a residual acidity of 10 mg KOH/g, and a surface area of 300 m²/g; and Filtrol grade 224, having virtually no moisture, and having a residual acidity of 3.0 mg KOH/g, and a surface area of 350 m²/g.

Preferably, the catalyst is activated by heat treatment before running the reaction. Applicants have found, surprisingly, that heat treatment of the catalyst prior to running the co-oligomerization reaction causes the catalyst to be more active and produce a higher olefin conversion. Additionally, clays heat treated in this manner are more stable, remaining active during the co-oligomerization reaction for a longer period of time. The clays may be heat treated at temperatures in the range of about 50° to 400° C., with or without the use of a vacuum. A more preferred temperature range is 50° to 300° C. Optionally, an inert gas may be used during heat treatment as well. Preferably, the clay should be heat treated under conditions and for a length of time which will reduce the water content of the clay to approximately 1 wt. % or less.

The co-oligomerization reaction may be carried out in either a stirred slurry reactor or in a fixed bed continuous flow reactor. The catalyst concentration should be sufficient to provide the desired catalytic effect. The temperatures at which the co-oligomerization may be performed are between about 50° and 300° C., with the preferred range being about 150° to 180° C. The reaction may be run at pressures of from 0 to 1000 psig.

Following the co-oligomerization reaction, the unsaturated oligomers may be hydrogenated to improve their thermal stability and to guard against oxidative degradation during their use as lubricants. The hydrogenation reaction for decene oligomers may be represented as follows:

$$C_{10n}H_{20n} + H_2 \xrightarrow{catalyst} C_{10n}H_{(20n+2)}$$

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The monomer stripping step should be conducted under mild conditions. Distillation at temperatures exceeding 250° C. may cause the oligomers to break down in some fashion and come off as volatiles. Preferably, therefore, the reboiler or pot temperature should be kept at or under about 225° C. when stripping out the unreacted monomer.

The invention will be further illustrated by the following examples, which are given by way of illustration and not as limitations on the scope of this invention.

EXAMPLES

The examples detailed in the table below demonstrate the use of the present invention in batch reaction systems:

Procedure

Olefin and Harshaw/Filtrol Clay-13 catalyst (40 g) were charged to a flask equipped with a stirrer, thermometer, heating mantle, and a water-cooled condenser (N₂ purge). The mixture was vigorously stirred and heated to a desired temperature for the desired time. The mixture was then cooled to ambient temperature and filtered with suction. The liquid was analyzed by liquid chromatography. Olefin conversion and dimer/trimer ratio were determined and are detailed in the table below.

Hydrogenation of Oligomer

An autoclave was charged with oligomer and finely powdered nickel catalyst. The autoclave was flushed with hydrogen and then pressured to 1000 psig with hydrogen. The mixture was heated to 200° C. and stirred at this temperature for 4 hours. The mixture was then repressured with hydrogen to 2000 psig as needed. The mixture was then cooled to ambient temperature, the catalyst was filtered and unreacted monomer was removed. Properties of the resulting synthetic lubricant base stocks are shown in the table below.

fins and internal-olefins, in the presence of an acidic calcium montmorillonite clay having a moisture content ranging up to about 20 wt. %, a residual acidity in the range of about 3 to about 30 mg KOH/g, and a surface area of about 300 m²/g or greater.

2. The process of claim 1, wherein the moisture content of the clay is about 12 wt. %, the residual acidity is about 8.5 mg KOH/g, and the surface area is about 425 m²/g.

3. The process of claim 1, wherein the moisture content of the clay is about 2 wt. %, the residual acidity is about 7.0 mg KOH/g, and the surface area is about 400 m²/g.

4. The process of claim 1, wherein the moisture content of the clay is about 16 wt. %, the residual acidity is about 15 mg KOH/g, and the surface area is about 300 m²/g.

5. The process of claim 1, wherein the moisture con-

| | | | | | | | Properties After Hydrogenation | | | | |
|---|---|---|---|---|---|---|---|---|---|---|---|
| Ex. No. | Olefin | (g) of Olefin | Wt. % Olefin As Vinylidene | Time/Temp (Hr)/(°C.) | Con. (%) of Olefin | D/T+ Ratio | Viscosity @ 210° F. (cSt) | Vis. Index | Noack (%) | CCSIM (cp) | Pour Point (°F.) |
| 1 | 1416α[1] | 400 | 20 | 5/160 | 81.4 | 1.58 | 5.43 | 139 | 13.7 | 800 | −20 |
| 2 | 1416α | 400 | 20 | 2/160 2/180 | 82.3 | 1.60 | 5.59 | 135 | 14.3 | 855 | −25 |
| 3 | 1416α | 400 | <5 | 5/160 | 85.0 | 1.28 | 6.08 | 140 | 12.0 | 880 | −10 |
| 4 | 1416α | 400 | <5 | 2/160 2/180 | 84.0 | 1.13 | 6.04 | 119 | 10.0 | 1015 | −5 |
| 5 | 16α[2] | 400 | <5 | 2/160 2/180 | 84.0 | 1.32 | 7.17 | 137 | 8.3 | 1550 | +15 |
| 6 | 16α/ 14-vin. | 380/ 20 | 5 | 2/160 2/180 | 81.1 | 1.64 | 6.46 | 140 | 7.4 | 1077 | +5 |
| 7 | 16α/ 14-vin. | 360/ 40 | 10 | 2/160 2/180 | 91.6 | 0.79 | 5.92 | 142 | 8.4 | 888 | 0 |
| 8 | 1518I[3]/ 14-vin. | 320/ 80 | 20 | 5/160 | 42.6 | 4.67 | 5.53 | 123 | * | * | −20 |

CO-OLIGOMERIZATION OF VINYLIDENE OLEFIN AND ALPHA- OR INTERNAL-OLEFIN[4]

Vin. = vinylidene; Con. = Conversion; I = Internal; Vis. = Viscosity; * = not determined; D = Dimer; T+ = Trimer + Tetramer + Pentamer, etc.; CCSIM = cold crank simulation; and cp = centipoise.
[1]From Ethyl Corporation: 1.3% $C_{12}$; 64.7% $C_{14}$; 33.0% $C_{16}$; and 1.0% $C_{18}$; containing approx. 19% of total olefin in vinylidene form.
[2]From Shell Chemical Co.: approx. 55% $C_{14}$ and 45% $C_{16}$; containing approx. 94.9% in alpha form and less than 5% in vinylidene form.
[3]Shell Chemical Co. Neodene ® 1518 Internal Olefin: 1.8% $C_{14}$ and lower; 25.3% $C_{15}$; 26.3% $C_{16}$; 24.2% $C_{17}$; 18.5% $C_{18}$; and 3.9% $C_{19}$.
[4]The catalyst for each of examples 1 through 8 was Harshaw/Filtrol Clay-13 (40 g).

The following example demonstrates the use of the present invention in continuous reaction systems. A 500 cc stainless steel reactor was charged with Harshaw/Filtrol Clay-24 and then heated for three days with a nitrogen purge (to drive off $H_2O$). The reactor was cooled to reaction temperature (155° C.) and a 1416α olefin mix containing 20% vinylidene olefin (determined by NMR) was pumped through the catalyst bed at a rate of 80 g/hour.

Initially, the reactor effluent showed. 77.7 % conversion and a dimer/trimer+ratio of 1.44. After four weeks, the conversion had dropped to 37.5%. Monomer was distilled off to give 6 gallons of material. The "bottoms" product was reduced with nickel catalyst to give a lubricant with the following properties:

| Viscosity (210° F.) | 5.32 cSt |
|---|---|
| Viscosity Index | 120 |
| Pour Point (°F.) | −50 |
| CCSIM (−20° C.) | 859 cp |
| Noack (250° C.) | 14.4% |

We claim:

1. A process for the preparation of a synthetic lubricant base stock, comprising co-oligomerizing a mixture of (1) a $C_{10}$ to $C_{24}$ vinylidene olefin and (2) a $C_{10}$ to $C_{24}$ olefin selected from the group consisting of alpha-oletent of the clay is about 4 wt. %, the residual acidity is about 10 mg KOH/g, and the surface area is about 300 m²/g.

6. The process of claim 1, wherein the moisture content of the clay is essentially nil, the residual acidity is about 3.0 mg KOH/g, and the surface area is about 350 m²/g.

7. The process of claim 1, wherein from about 5 to about 40 wt. % of the mixture to be co-oligomerized comprises $C_{10}$ to $C_{24}$ vinylidene olefin.

8. The process of claim 1, wherein about 20 wt. % of the mixture to be co-oligomerized comprises $C_{10}$ to $C_{24}$ vinylidene olefin.

9. The process of claim 1, wherein the $C_{10}$ to $C_{24}$ olefin selected from the group consisting of alpha-olefins and internal-olefins is an alpha-olefin.

10. A process for the preparation of a synthetic lubricant base stock, comprising co-oligomerizing a mixture of (1) a $C_{14}$ to $C_{18}$ a vinylidene olefin and (2) a $C_{14}$ to $C_{18}$ a olefin selected from the group consisting of alpha-olefins and internal-olefins, in the presence of an acidic calcium montmorillonite clay having a moisture content ranging up to about 20 wt. %, a residual acidity in the range of about 3 to about 30 mg KOH/g, and a surface area of about 300 m²/g or greater.

11. The process of claim 10, wherein the moisture content of the clay is about 12 wt. %, the residual acidity is about 8.5 mg KOH/g, and the surface area is about 425 m$^2$/g.

12. The process of claim 10, wherein the moisture content of the clay is about 2 wt. %, the residual acidity is about 7.0 mg KOH/g, and the surface area is about 400 m$^2$/g.

13. The process of claim 10, wherein the moisture content of the clay is about 16 wt. %, the residual acidity is about 15 mg KOH/g, and the surface area is about 300 m$^2$/g.

14. The process of claim 10, wherein the moisture content of the clay is about 4 wt. %, the residual acidity is about 10 mg KOH/g, and the surface area is about 300 m$^2$/g.

15. The process of claim 10, wherein the moisture content of the clay is essentially nil, the residual acidity is about 3.0 mg KOH/g, and the surface area is about 350 m$^2$/g.

16. The process of claim 10, wherein from about 5 to about 40 wt. % of the mixture to be co-oligomerized comprises $C_{14}$ to $C_{18}$ vinylidene olefin.

17. The process of claim 10, wherein about 20 wt. % of the mixture to be co-oligomerized comprises $C_{14}$ to $C_{18}$ vinylidene olefin.

18. The process of claim 10, wherein the $C_{14}$ to $C_{18}$ olefin selected from the group consisting of alpha-olefins and internal-olefins is an alpha-olefin.

19. A process for the preparation of a synthetic lubricant base stock, comprising: co-oligomerizing a mixture of (1) a $C_{10}$ to $C_{24}$ vinylidene olefin and (2) a $C_{10}$ to $C_{24}$ alpha-olefin by contacting said mixture with an acidic calcium montmorillonite clay having a moisture content ranging up to about 20 wt. %, a residual acidity in the range of about 3 to about 30 mg KOH/g, and a surface area of about 300 m$^2$/g or greater; separating out any remaining un-oligomerized olefin; and hydrogenating the resulting oligomer fraction to produce a synthetic lubricant base stock.

20. The process of claim 19, wherein the vinylidene olefin contains from 14 to 18 carbon atoms, and the alpha-olefin contains from 14 to 18 carbon atoms.

* * * * *